(12) United States Patent
Rabiner et al.

(10) Patent No.: US 6,551,337 B1
(45) Date of Patent: Apr. 22, 2003

(54) ULTRASONIC MEDICAL DEVICE OPERATING IN A TRANSVERSE MODE

(75) Inventors: Robert A. Rabiner, North Reading, MA (US); Brad A. Hare, Chelmsford, MA (US); David M. Fischer, Waltham, MA (US); Andy Levine, Newton Centre, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 210 days.

(21) Appl. No.: 09/618,352

(22) Filed: Jul. 19, 2000

Related U.S. Application Data

(60) Provisional application No. 60/178,901, filed on Jan. 28, 2000, and provisional application No. 60/157,824, filed on Oct. 5, 1999.

(51) Int. Cl.⁷ .............................. A61B 17/32
(52) U.S. Cl. ..................... 606/169; 606/170; 606/171
(58) Field of Search ......................... 606/169, 170, 606/171, 177, 178, 180; 604/22

(56) References Cited

U.S. PATENT DOCUMENTS

| | | |
|---|---|---|
| 2,990,616 A | 7/1961 | Balamuth et al. |
| 3,526,219 A | 9/1970 | Balamuth |
| 3,565,062 A | 2/1971 | Kuris |
| 3,589,363 A | 6/1971 | Banko et al. |
| 3,805,787 A | 4/1974 | Banko |
| 3,861,391 A | 1/1975 | Antonevich et al. |
| 4,136,700 A | 1/1979 | Broadwin et al. |
| 4,236,510 A | 12/1980 | Hatter et al. |
| 4,474,180 A | 10/1984 | Angulo |
| 4,486,680 A | 12/1984 | Bonnet et al. |
| 4,493,694 A | 1/1985 | Wuchinich |
| 4,504,264 A | 3/1985 | Kelman |
| 4,526,571 A | 7/1985 | Wuchinich |
| 4,535,759 A | 8/1985 | Polk et al. |
| 4,634,420 A | 1/1987 | Spinosa et al. |
| 4,838,853 A | 6/1989 | Parisi |
| 4,867,141 A | 9/1989 | Nakada et al. |
| 4,870,953 A | 10/1989 | DonMichael et al. |
| 4,886,060 A * | 12/1989 | Wiksell ........................ 604/22 |

(List continued on next page.)

FOREIGN PATENT DOCUMENTS

| | | |
|---|---|---|
| EP | 0 293 472 | 12/1988 |
| EP | 0 541 249 | 5/1993 |
| WO | WO 90/01300 | 2/1990 |
| WO | WO 95/03740 | 2/1995 |
| WO | WO 96/07377 | 3/1996 |
| WO | WO 98/35721 | 8/1998 |
| WO | WO 98/55032 | 12/1998 |
| WO | WO 99/33404 | 7/1999 |
| WO | WO 99/35982 | 7/1999 |
| WO | WO 00/21444 | 4/2000 |

*Primary Examiner*—Michael J. Milano
*Assistant Examiner*—Jessica Baxter
(74) *Attorney, Agent, or Firm*—Palmer & Dodge, LLP; Richard B. Smith

(57) ABSTRACT

An ultrasonic medical device comprises an ultrasonic vibration generator that generates vibration along its longitudinal axis. The ultrasonic vibration is transmitted through an ultrasonic coupler and a series of transformer sections that amplify the ultrasonic vibration. A flexible member is coupled to the distal end of the transformer sections, and is thus supplied with a longitudinal vibration at its base by the transformer sections. The flexible member is designed so that it converts the longitudinal vibration into a standing wave that runs along the length of the flexible member. The standing wave produces a series of nodes and anti-nodes along the length of the flexible member. Each of the anti-nodes produces cavitation in fluids in contact with the probe. The cavitation of the fluids causes destruction of adjacent tissue. In this manner, the entire length of the flexible member becomes a working surface that may be utilized for destroying tissue.

57 Claims, 4 Drawing Sheets

U.S. PATENT DOCUMENTS

| | | |
|---|---|---|
| 4,886,491 A | 12/1989 | Parisi et al. |
| 4,920,954 A | 5/1990 | Alliger et al. |
| 4,922,902 A | 5/1990 | Wuchinich et al. |
| 4,931,047 A | 6/1990 | Broadwin et al. |
| 4,961,424 A | 10/1990 | Kubota et al. |
| 4,962,755 A | 10/1990 | King et al. |
| 4,989,583 A | 2/1991 | Hood |
| 5,015,227 A | 5/1991 | Broadwin et al. |
| 5,026,387 A | 6/1991 | Thomas |
| 5,057,119 A | 10/1991 | Clark et al. |
| 5,057,182 A | 10/1991 | Wuchinich |
| 5,059,210 A | 10/1991 | Clark et al. |
| 5,062,827 A | 11/1991 | Wiksell |
| 5,112,300 A | 5/1992 | Ureche |
| 5,116,343 A | 5/1992 | Ams et al. |
| 5,163,421 A | 11/1992 | Bernstein et al. |
| 5,167,619 A | 12/1992 | Wuchinich |
| 5,171,387 A | 12/1992 | Wuchinich |
| 5,176,677 A | 1/1993 | Wuchinich |
| 5,180,363 A | 1/1993 | Idemoto et al. |
| 5,190,517 A | 3/1993 | Zieve et al. |
| 5,221,282 A | 6/1993 | Wuchinich |
| 5,243,997 A | 9/1993 | Uflacker et al. |
| 5,267,954 A | 12/1993 | Nita |
| 5,269,297 A | 12/1993 | Weng et al. |
| 5,271,735 A | 12/1993 | Greenfield et al. |
| 5,300,021 A | 4/1994 | Wuchinich |
| 5,304,115 A | 4/1994 | Pflueger, Russell et al. |
| 5,312,328 A | 5/1994 | Nita et al. |
| 5,312,329 A | 5/1994 | Beaty et al. |
| 5,324,299 A | 6/1994 | Davison et al. |
| 5,334,183 A | 8/1994 | Wuchinich |
| 5,342,292 A | 8/1994 | Nita et al. |
| 5,358,505 A | 10/1994 | Wuchinich |
| 5,366,490 A | 11/1994 | Edwards et al. |
| 5,368,558 A | 11/1994 | Nita |
| 5,380,274 A | 1/1995 | Nita |
| 5,382,228 A | 1/1995 | Nita et al. |
| 5,391,144 A * | 2/1995 | Sakurai et al. ................ 604/22 |
| 5,397,293 A | 3/1995 | Alliger et al. |
| 5,397,301 A | 3/1995 | Pflueger et al. |
| 5,405,318 A | 4/1995 | Nita |
| 5,417,654 A | 5/1995 | Kelman |
| 5,417,672 A | 5/1995 | Nita et al. |
| 5,427,118 A | 6/1995 | Nita et al. |
| 5,447,509 A | 9/1995 | Mills et al. |
| 5,458,612 A | 10/1995 | Chin |
| 5,472,441 A | 12/1995 | Edwards et al. |
| 5,484,398 A | 1/1996 | Stoddard |
| 5,498,236 A | 3/1996 | Dubrul et al. |
| 5,516,043 A | 5/1996 | Manna et al. |
| 5,603,445 A | 2/1997 | Hill et al. |
| 5,628,743 A | 5/1997 | Cimino |
| 5,630,837 A | 5/1997 | Crowley |
| 5,672,172 A | 9/1997 | Zupkas |
| 5,713,848 A | 2/1998 | Dubrul et al. |
| 5,720,710 A | 2/1998 | Tachibana et al. |
| 5,725,494 A | 3/1998 | Brisken |
| 5,728,062 A | 3/1998 | Brisken |
| 5,735,811 A | 4/1998 | Brisken |
| 5,741,225 A | 4/1998 | Lax et al. |
| 5,772,627 A | 6/1998 | Acosta et al. |
| 5,827,203 A | 10/1998 | Nita |
| 5,836,896 A | 11/1998 | Rosenschein |
| 5,836,897 A | 11/1998 | Sakurai et al. |
| 5,843,017 A | 12/1998 | Yoon |
| 5,846,218 A | 12/1998 | Brosken et al. |
| 5,891,149 A | 4/1999 | Young et al. |
| 5,895,370 A | 4/1999 | Edwards et al. |
| 5,931,805 A | 8/1999 | Brisken |
| 5,935,096 A | 8/1999 | Barrett |
| 5,935,142 A | 8/1999 | Hood |
| 5,957,882 A | 9/1999 | Nita et al. |
| 5,964,756 A | 10/1999 | McGaffigan et al. |
| 5,989,208 A | 11/1999 | Nita |
| 5,989,209 A | 11/1999 | Barrett |
| 5,989,274 A | 11/1999 | Davison et al. |
| 6,032,078 A | 2/2000 | Rudie |
| 6,077,285 A | 6/2000 | Boukhny |

\* cited by examiner

ULTRASONIC MEDICAL DEVICE OPERATING IN A TRANSVERSE MODE

This application claims benefit to U.S. provisional application Ser. No. 60/178,901 filed Jan. 28, 2000 which claims benefit to U.S. provisional application Ser. No. 60/157,824, filed Oct. 5, 1999.

BACKGROUND OF THE INVENTION

1. Field of the Invention

The present invention relates generally to medical devices, and more particularly to an ultrasonic medical device for destroying tissue in a controlled fashion within a human body.

2. Description of Related Art

Medical instruments utilizing ultrasonic energy to destroy tissue in a human body are known in the art. One drawback of existing ultrasonic medical instruments which remove tissue is that typically doctors have considered them to be slow in comparison to methods such as surgical excision. Part of the reason for this perceived slowness is explained by the fact that most existing ultrasonic devices rely on a longitudinal vibration of the tip of the probe. In other words, the tip of the probe is vibrated in a direction in line with the longitudinal axis of the probe. This produces a tissue destroying affect only at the tip of the probe.

One solution that has been proposed is to vibrate the tip of the probe in a transverse direction—i.e. perpendicular to the longitudinal axis of the probe—in addition to vibrating the tip in the longitudinal direction. For example, U.S. Pat. No. 4,961,424 to Kubota et al. discloses an ultrasonic treatment device to destroy and emulsify concretions or tissue in a human body. The Kubota et al. device produces both a longitudinal and transverse motion at the tip of the probe. The Kubota et al. patent, however, still relies solely on the tip of the probe to act as a working surface. Therefore, it improves the efficiency of the tip, but still relies on the tip of the probe to perform all cutting actions.

Although Kubota et al. describe providing a transverse motion at the tip of the probe, a transverse motion along the length of the probe has generally been discouraged. For example, U.S. Pat. No. 4,474,180 to Angulo discloses an ultrasonic kidney stone disintegration instrument with a damping material applied to the wire probe to inhibit lateral vibrations of the wire in the region of the connection to the ultrasonic transducer.

Another proposed method of improving the speed of ultrasonic tissue remove is oscillating the tip of the probe in addition to longitudinally vibrating the tip of the probe. For example, U.S. Pat. No. 4,504,264 to Kelman discloses an ultrasonic treatment device which improves the speed of ultrasonic tissue removal. In the Kelman device, the tip of the probe is vibrated longitudinally and also oscillated, so that the cutting efficiency of the probe tip is improved. Again, however, only the tip of the probe performs a cutting action.

BRIEF SUMMARY OF THE INVENTION

The object of the present invention is to provide an ultrasonic medical device capable of destroying and emulsifying tissue through cavitation in the human body with a higher efficiency by means of a flexible probe operating in a transverse mode. As used herein, a transverse mode of operation is used to describe a flexible probe with a plurality of nodes and anti-nodes along the length of the probe.

In accordance with this object, an ultrasonic medical device comprises an ultrasonic vibration generator that generates vibration along its longitudinal axis. The ultrasonic vibration is transmitted through an ultrasonic coupler and a series of transformer sections that amplify the ultrasonic vibration. A flexible member is coupled to the distal end of the transformer sections, and is thus supplied with a longitudinal vibration at its base by the transformer sections. The flexible member is designed so that it converts the longitudinal vibration into a standing wave that runs along the length of the flexible member. The standing wave produces a series of nodes and anti-nodes along the length of the flexible member. Each of the anti-nodes produces cavitation in fluids in contact with the probe. The cavitation of the fluids causes destruction of adjacent tissue. Thus, in this manner, the entire length of the flexible member becomes a working surface that may be utilized for destroying tissue.

Therefore, in contrast to the prior art designs that only utilize a tip of a probe as a surface, the entire length of the flexible member forms a cutting surface in the present invention.

BRIEF DESCRIPTION OF THE INVENTION

DETAILED DESCRIPTION OF THE INVENTION

Figure 1:
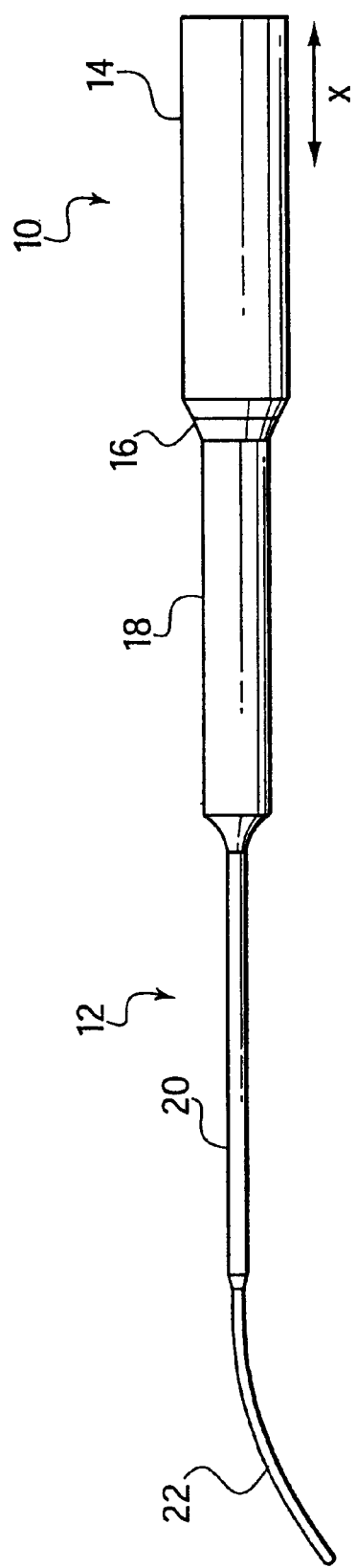
FIG. 1 shows a schematic view of an ultrasonic probe constructed in accordance with the principles of the invention.
Figure 2:
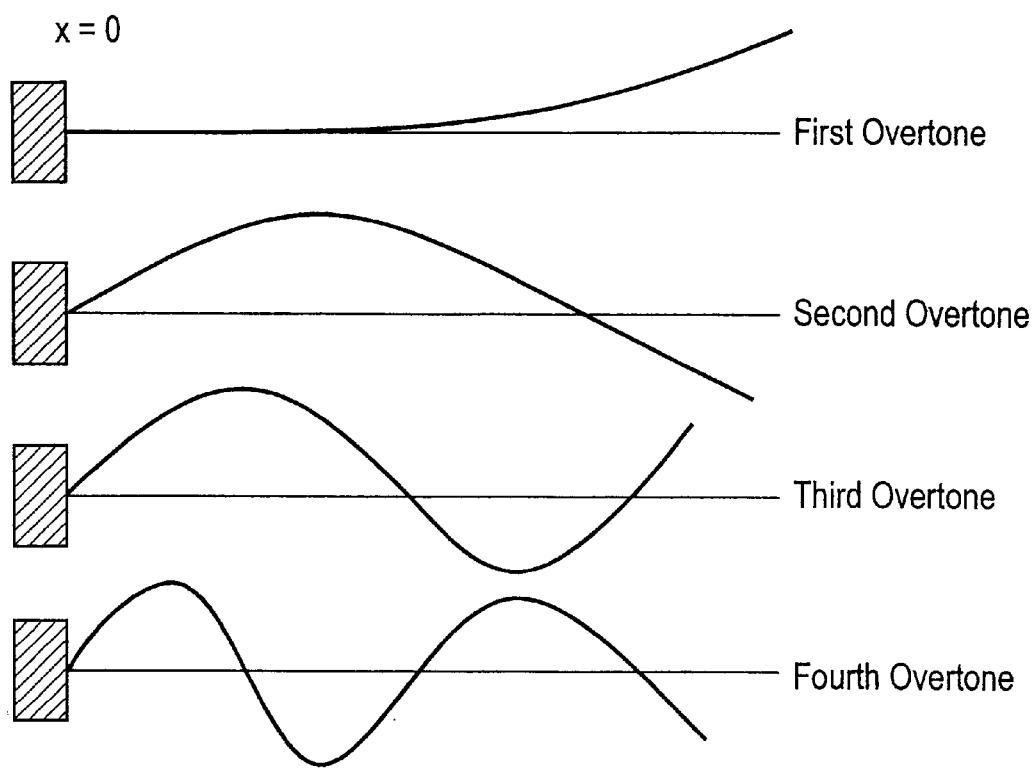
FIG. 2 shows the flexible member of the ultrasonic probe operating in a transverse mode.
Figure 3:
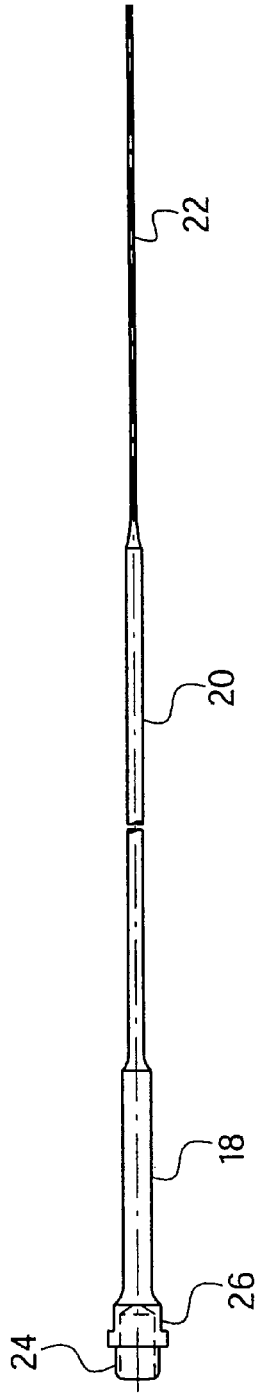
FIG. 3 shows a probe assembly for use in an ultrasonic probe constructed in accordance with the principles of the invention.

As seen in FIGS. 1 and 3, the ultrasonic probe has a handle section 10 and a probe section 12. The handle is formed by an ultrasonic driver 14 and an ultrasonic coupling horn 16. The ultrasonic driver has a longitudinal axis. The driver produces an ultrasonic vibration in the range of 20–80 kHz. The nominal driver amplitude is 50 microns at 100 volt peak to peak sinusoidal excitation. The vibration is along the direction of the longitudinal axis. In the embodiment illustrated, the transducer is PZT-4. However, the driver can utilize a variety of methods to produce an ultrasonic vibration, such as piezoelectric, magnetostrictive, pneumatic, or hydraulic, as are known to those skilled in the art. A control unit (not illustrated) controls the ultrasonic driver. The control unit allows an operator to adjust the frequency and amplitude of the vibration which is produced by the driver. In the exemplary embodiment illustrated here, the probe is designed to operate at a frequency of 20 kHz. However, the probe may be designed to operate at frequencies in the range of 20 kHz to 80 kHz, as described in detail in the theory of operation section.

The ultrasonic driver is coupled to a coupling horn 16, and the ultrasonic vibration is transmitted from the driver to the coupling horn. The coupling horn is connected to the probe section 12. The probe section has a series of transformer sections 18, 20. The transformer sections are a series of shafts constructed from any suitable material, such as Ti-6Al-4v titanium. The transformer sections transmit vibrations from the coupling horn to a flexible member 22 at the distal end of the probe section. In the process of transmission, the amplitude of the vibration is amplified by the transformer sections. The diameter of the transformer sections are chosen so as to produce a suitable amount of longitudinal vibration at the end of the transformer section. The gain of the transformer sections is controlled by the ratio of the area of the sections. In the exemplary embodiment described herein, the transformer sections are designed to produce a gain of about 4–5 over the transducer. This is achieved by setting the diameter of the transformer sections 18, 20 at 0.150 and 0.080 inches, respectively. The length of the transformer sections 18, 20 are 1.500 and 7.554 inches, respectively. The transformer section 18 has a threaded portion 24 to mate with the coupling horn 16, and has a portion 26 which is adapted so that it may be grasped with a wrench or another tool to tighten the connection.

A flexible member 22 is attached to the end of the last transformer section, and is driven by the last transformer section. The flexible member is a thin, wire like probe, typically less than 1 mm in diameter. In the embodiment shown, the flexible member has a circular cross-section with a diameter of 0.020 inches. The flexible member may have other cross-sections, such as a rectangular or oval cross-section. The flexible portion of the probe can be multiple wavelengths in length. In the embodiment shown, the flexible member is 4.046 inches long, which corresponds to a device operating with a frequency of approximately 20 kHz. The preferred material is 6Al-4v titanium; however, any other materials may be used as long as the operating parameters fall within the operation limits set by the strength of the material, as discussed in detail below.

Figure 4:
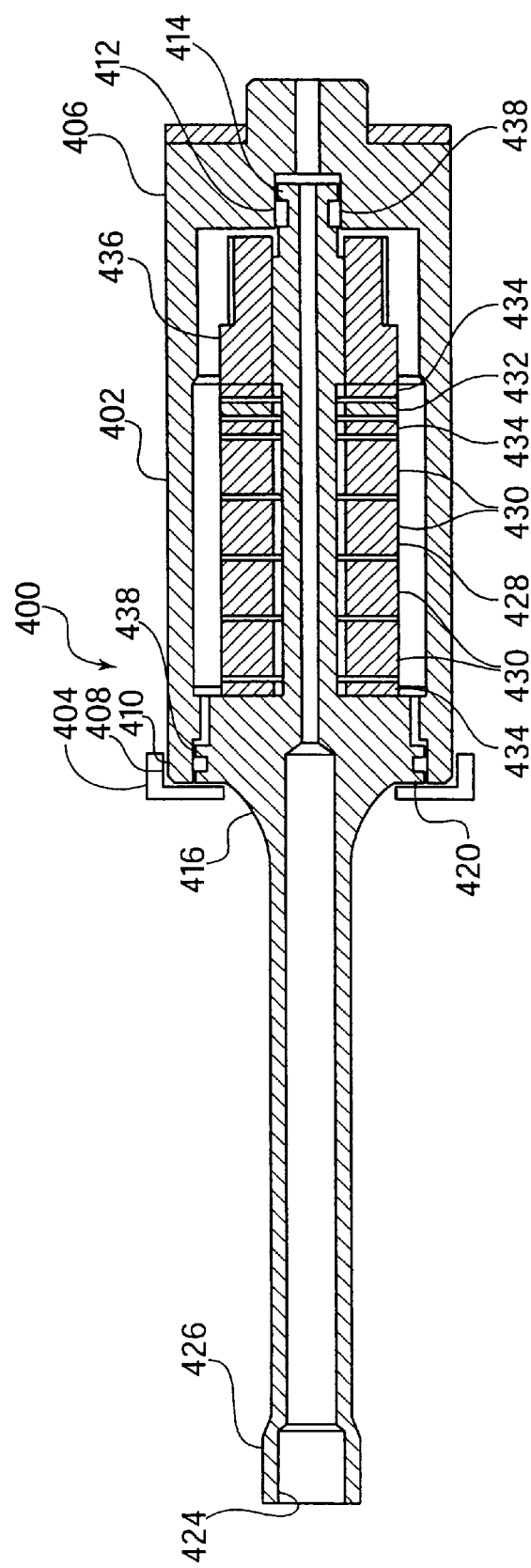
FIG. 4 shows a cross-sectional view of the handle assembly of an ultrasonic probe constructed in accordance with the principles of the invention.
Figure 5A:
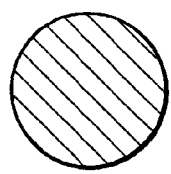
FIGS. 5A–5D show possible various cross-sectional profiles of a flexible member for use in the present invention.
Figure 5B:
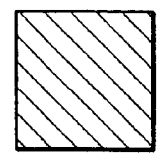
Figure 5C:
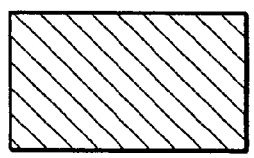
Figure 5D:
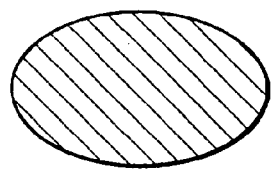

FIG. 4 shows a cross-sectional view of the handle assembly of an ultrasonic probe constructed in accordance with the principles of the invention. FIG. 4 shows an exemplary horn assembly 400 suitable for use in the present invention. A housing 402 has a end cap 404 and a rear portion 406. The end cap 404 has an internal threaded portion 408 which mates with an external threaded portion 410 of the rear portion 406. The rear portion 406 of the housing 402 has a recess 412 which receives an extended portion 414 of the horn 416. The end cap 404 is shaped as a ring with a opening 418. The horn 416 fits through the opening 418. A flange 420 on the horn 416 is larger than the opening 418 so that when the end cap 404 is screwed on, the horn 416 is held tightly into the housing 402. The horn 416 has female threads 424 at one end 426 to mate with a probe assembly. Grooves 438 are provided on the horn 416. O-rings (not shown) may be placed into the grooves to provide a substantially fluid-tight seal.

A stack of piezo-ceramic drivers 428 is arranged around the horn 416. The driver stack 428 has four driver ceramics 430, and an additional feedback ceramic 432. The feedback ceramic 432 is used to measure the driver amplitude. Each driver is provided with a nickel electrode for connection to an electrical source (not shown). The electrical source provides an alternating waveform at the appropriate frequency and amplitude. Insulators 434 are provided to isolate the piezo-ceramics from the horn and from the feedback ceramic. MACOR™ insulators, available from Corning, are one suitable type of insulator. The extended portion 414 of the horn 416 is threaded so that a nut 436 may be used to secure the piezo-ceramic drivers to the horn.

FIGS. 5A–5D show various cross-sectional profiles of ultrasonic probes which are suitable for use with the present invention. As will be discussed in detail later, any cross-sectional profile may be utilized so long as certain design constraints are met.

Figure 6:
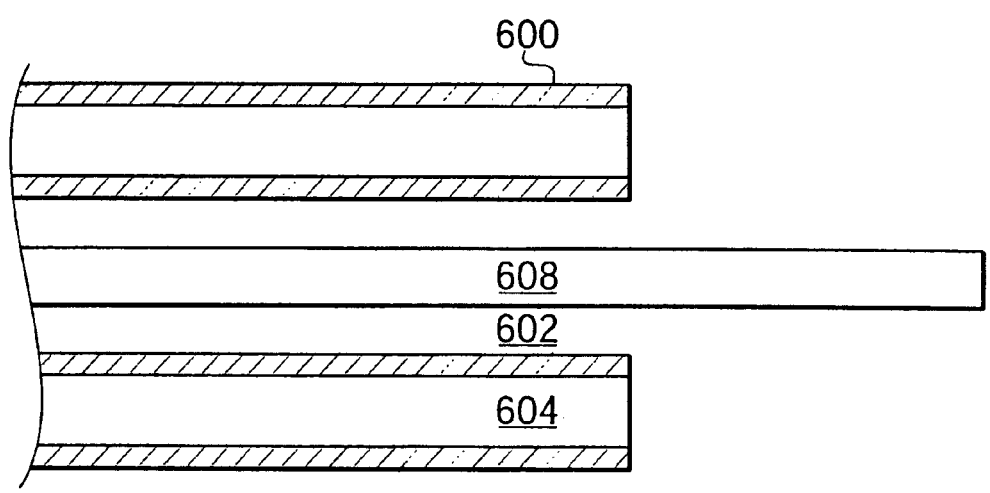
FIG. 6 shows the ultrasonic probe and an associated sheath.

As seen in FIG. 6, proximal to the desired, active length 606 of the probe 608, the probe 608 is placed within a sheath 600 which can provide irrigation channels and aspiration channels 602, 604. Irrigation is preferably provided between the probe 608 and the sheath 600. The sheath 600 is preferably made of PTFE or Teflon tubing so as to absorb the ultrasonic energy emanating from portions of the probe located within the sheath, thereby allowing control over the amount of tissue affected by the probe. The sheathing is not restricted to the preferred materials as long as it is made of a material which is not heated by the ultrasonic energy, although the irrigation fluid can be used to cool the sheath material. The probe may be extended or retracted from the sheath to modify the amount of probe exposed, thereby modifying the active length 606 of the probe. Further details regarding one suitable sheath are described in Applicant's co-pending application Ser. No. 60/157,824, which is hereby incorporated by reference.

THEORY OF OPERATION OF THE INVENTION

Although, not intended to be bound by the following theory of operation, it is believed that the following theory describes the operation of the ultrasonic probe of the present invention. In operation, the longitudinal push delivered by the transformer sections causes a flexing or buckling of the thin member at the end of the probe. The buckling may be realized as a flexure or standing transverse wave along the length of the probe section. The flexure case is simply the first order transverse mode of vibration as will be described below.

In a fluid or fluid containing medium, each of the antinodes (positions corresponding to maximum transverse displacement) along the length of the probe cause cavitation of the fluid in a direction perpendicular to the longitudinal axis of the probe. Cavitation is a void or bubble produced by the inability of the fluid to overcome the stresses induced by the motion of the probe. The collapse of the cavitation bubbles in and around cellular (or biological) material produces a shockwave that erodes or fragments the material allowing it to be removed through aspiration and suction. The mechanism of cavitation and its affect on tissues is well known in the art, and is described in such literature as U.S. Pat. No. 3,526,219 to Balamuth.

The equations of motion governing the operation of the are obtained by applying Newton's second law to the forces and accelerations acting upon an infinitesimal segment. The equation of motion for the transverse oscillations of a thin member (neglecting losses in the material and surroundings) is then given by:

$$\frac{\partial^4 \xi}{\partial X^4} + \frac{1}{(\kappa c)^2} \frac{\partial^2 \xi}{\partial t^2} = 0 \qquad 2.0$$

Where x is the distance along the flexible portion, t is the time in seconds ξ is the transverse displacement, κ is the radius of gyration, and c is the speed of sound in the material.

In can be shown for boundary conditions which assume a flexible member of length l fixed at one end and free at the other, the general solution to this equation will have the form:

$$\xi = \cos(\omega t + \phi_n)\left(A\left(\cosh\omega\frac{X}{v} - \cos\omega\frac{X}{v}\right) + B\left(\sinh\omega\frac{X}{v} - \sin\omega\frac{X}{v}\right)\right) \quad 2.1$$

Applying the boundary conditions it can be shown that $$\cot\left(\frac{\omega l}{2v}\right)\tanh\left(\frac{\omega l}{2v}\right) = 1 \quad 2.2$$

Where $\omega$ is the angular frequency in radians per second, x is the distance along the flexible member (as before) and v is the phase velocity given by:

$$v = \sqrt{\omega c \kappa} \quad 2.3$$

Here c is the longitudinal propagation velocity given by:

$$c = \sqrt{Y/\rho} \quad 2.4$$

where Y is Young's modulus and $\rho$ is the density of the material.

The solutions of equations 2.2 only occur at discrete frequencies, which for the first four overtones can be shown to be:

$$f_n = \frac{\pi c \kappa A_n}{8l^2} \quad 2.5$$

The $A_n$ terms are the solutions to equation 2.2. For the nth overtone they are $(1.194)^2, (2.988)^2, (5)^2, (7)^2 \ldots (2n-1)^2$ For overtones of the fundamental the node positions along the flexible member can be derived from the general solution given in equation 2.1. The nodal positions are the points at which the displacements and the bending moment are zero:

$$\xi_n = 0, \quad \frac{\partial^2 \xi_n}{\partial X^2} = 0$$

with $$\frac{\partial^2 \xi_n}{\partial X^2} = \cos(\omega t + \phi)\left(\frac{\omega}{v}\right)^2\left(A\left(\cosh\omega\frac{X}{v} + \cos\omega\frac{X}{v}\right) + B\left(\sinh\omega\frac{X}{v} + \sin\omega\frac{X}{v}\right)\right) \quad 2.6$$

Using equations 2.1 and 2.6 it can be shown that:

$$\tan\omega\frac{X}{v} = \tanh\omega\frac{X}{v} \quad 2.7$$

which has solutions for:

$$\frac{\omega}{v} = \frac{\pi}{2l}(5, 7, 9 \ldots) \quad 2.8$$

The positions of the nodes for a member of length l will then be:

| | |
|---|---|
| First overtone: | x = 0 |
| Second overtone | x = 0, x = 0.7741 |
| Third overtone | x = 0, x = 0.51, x = 0.8681 |
| Fourth overtone | x = 0, x = 0.3561, x = .6441, x = .9051 |
| Etc . . . | |

Figure Two shows the flexible portion oscillating in modes up to the fourth overtone.

For a practical design the forces acting on the flexible member have to be kept within safe limits for the material chosen. The bending moment of the flexible member is given by the equation:

$$M = YA\kappa^2 \frac{\partial^2 \xi}{\partial x^2} \quad 3.0$$

with A being the cross sectional area of the flexible member. Equation 3.0 will be recognized immediately as the standard differential equation for a beam in flexure.

The shear force acting along the member will be given by the equation:

$$F_s = \frac{\partial M}{\partial x} = YA\kappa^2 \frac{\partial^3 \xi}{\partial x^3} \quad 3.1$$

The preferred embodiment is a probe of circular cross section as described; however alternate shapes could be used as long as certain design constraints are considered. The key parameter is the $Y\kappa^2$ term appearing in equations 3.0 and 3.1, often referred to as the flexural stiffness. For annealed Ti-6AL-4V titanium optimal values are in the range $2.5\times10^7$ to $8.5\times10^7$ N/m. Note that the use of the flexural stiffness as a design parameter allows a shape independent specification for flexible member.

The driver and transformer sections are designed to provide sufficient longitudinal amplitude to support the desired transverse mode amplitude (see section on design constraints below). Typically the handle and probe assembly are designed to support a longitudinal amplitude which will be sufficient to induce buckling in the flexible member. The length of the entire probe and handle assembly is chosen to place a longitudinal anti-node at the end of the flexible member. This restricts the length of the handle and tip assembly to integer multiples of one half the longitudinal wavelength. In actual practice it has been found that a slight de-tuning of around 3 to 5 percent aids the conversion to the transverse mode. It should be noted that there is no longitudinal vibration of the tip as this is converted entirely into a transverse vibration through buckling of the thin member at the tip.

The force, or longitudinal push, imparted to the flexible member by the longitudinal section must be sufficient to induce buckling. The maximum longitudinal force exerted at startup must meet the Euler conditions for buckling, which are the solutions to equation 3.0, yielding the formula for the critical force:

$$P_{crit} = \frac{n^2\pi^2 Y\kappa^2}{l^2}, \quad (n = 1, 2, 3 \ldots) \quad 3.2$$

For the longitudinal drive the maximum stress at startup will be:

$$s = \frac{2\pi Y f \xi_m}{c} \qquad 3.3$$

Where $\xi_m$ is the maximum longitudinal displacement of the assembly (probe and handle), f is the drive frequency, c is the longitudinal propagation velocity (Eq. 2.4) and Y is Young's modulus for the material.

An optimal design will try to place as many anti-nodes as possible along the length of the flexible member. In the exemplary embodiment described and illustrated before, with a 3.748 inch long flexible member with a diameter of 0.020 inches, 6 nodes are produced at a frequency of 20 kHz.

The proceeding equations show that the stresses on the material increase with frequency. When coupled with the need to produce sufficient amplitude to remove tissue upper bounds for frequency can be established. To produce cavitation in fluid the transverse amplitude should be at least 75 microns. This will limit the frequency to about 80 kHz for 6Al-4V titanium (this disregards material losses which must be experimentally determined). The lower limit for the frequency is usually chosen to be outside of the range of human hearing, or greater than 20 kHz.

The transverse mode probe is much more effective at tissue removal than are the longitudinal designs of the prior art. One reason for this is because the action of the energy is along most of the length of the exposed flexible member and is not confined to the surface area of the tip of the member. The probes described in the prior art which are only driven in the longitudinal direction only work at the tip. Even with a solid tip, its active area in contact with tissue is much less than the transverse mode tip. Also, the tissue destruction of the transverse mode probes extends up to 1 mm circumferentially beyond the probe. The following calculations indicate the efficacy of the transverse mode compared to a standard longitudinal probe.

A rigid, solid, 4 mm probe works only at the tip. As it moves forward and back, it cavitates the fluid in front of it. The volume of tissue effected is:

| Frequency | f | 20,000 hz | |
|---|---|---|---|
| Stroke | $\Delta x$ | 350 microns (.35 mm) | |
| Radius | r | 2 mm | |
| Cross sectional area | $A_x$ | $\pi r^2$ | 12.6 mm$^2$ |
| Volume of tissue removed per stroke | V | $A_x * \Delta x$ | 4.40 mm$^3$ |
| Volume of tissue removed per time | $V_t$ | V*f/60/1,000 | 1.47 cc/min |

For a 2 cm long by 0.5 mm diameter probe working in the transverse mode:

| Frequency | f | 20,000 hz | |
|---|---|---|---|
| Radius | r | 0.25 mm | |
| Effective radius | $r_e$ | 1.25 mm | |
| Effective length | L | 20 mm | |
| Cross sectional area | $A_x$ | $\pi r_e^2$ | 4.91 mm$^2$ |
| Volume of tissue removed per stroke | V | $A_x * L$ | 98.1 mm$^3$ |
| Volume of tissue removed per time | $V_t$ | V*f/60/1,000 | 32.7 cc/min |

This means that in these circumstances, the transverse mode tip removes tissue at a rate 22.2 times faster than the solid tip working in the longitudinal mode. Also, the transverse mode flexible member is typically $\frac{1}{8}^{th}$ the size of the longitudinal probe. Comparing two, 0.5 mm probes, one working in the longitudinal mode and one in the transverse mode, the transverse mode tip removes tissue 1,428 times faster than the longitudinal probe.

The transverse mode probe is capable of maintaining its vibration when bent if the sum of the stresses imposed by the transverse vibration and the bending stresses do not exceed the elastic limit of the material. This offers significant advantages over longitudinal mode designs that are typically rigid over their entire length.

What is claimed is:

1. An ultrasonic medical device comprising:
   an ultrasonic generator for producing an ultrasonic vibration in a direction along a longitudinal axis of the ultrasonic generator;
   an ultrasonic coupling horn;
   at least one transformer section ultrasonically coupled to the ultrasonic source by the ultrasonic coupling horn, the transformer section modifying the amplitude of the ultrasonic vibration; and
   a flexible member driven by the transformer section wherein the flexible member has a degree of stiffness which allows the flexible member to support a transverse ultrasonic vibration,
   wherein the transverse ultrasonic vibration along a length of the flexible member produces a plurality of transverse nodes and anti-nodes along the length of the flexible member wherein at least a portion of the length of the flexible member is used in a medical procedure, wherein more than one of the plurality of transverse anti-nodes are in communication with a biological material.

2. A device according to claim 1, wherein the ultrasonic generator produces an ultrasonic vibration in the range of about 20 khz to about 80 khz.

3. A device according to claim 1, wherein the ultrasonic generator produces an ultrasonic vibration of approximately 20 khz.

4. A device according to claim 3, wherein a length of the flexible member is chosen so that eight nodes are produced along the length of the flexible member.

5. A device according to one of claims 1–4, wherein the flexible member is a thin, flexible member capable of being deflected and articulated when the device is in operation.

6. A device according to claim 5, wherein at least one transformer section is formed of one of the following materials: titanium, aluminum, or steel.

7. A device according to one of claims 1–4, wherein the flexible member is formed of one of the following materials: titanium, aluminum, or steel.

8. A device according to one of claims 1–4, wherein the transformer section is sized so that it produces a gain of about 4–5 over a transducer.

9. A device according to claim 1, wherein the flexible member has a circular cross-section.

10. A device according to claim 9, wherein the flexible member has a diameter of less than about 1 mm.

11. A device according to claim 9, wherein the flexible member has a diameter of about 0.020 inches.

12. A device according to claim 9, wherein the flexible member has a diameter of about 0.030 inches.

13. A device according to claim 1, wherein the flexible member has a square cross-section.

14. A device according to claim 1, wherein the flexible member has a rectangular cross-section.

15. A device according to claim 1, wherein the flexible member has an elliptical cross-section.

16. A device according to claim 1, wherein the flexural stiffness of the flexible member is in the range of about $2.5 \times 10^7$ N/m to about $8.5 \times 10^7$ N/m.

17. A method of removing a biological material from a cavity in a human body, comprising the steps of:
   (a) providing a flexible member with a proximal end, a distal end and a longitudinal axis wherein the flexible member has a degree of stiffness which allows the flexible member to support a transverse ultrasonic vibration;
   (b) providing an ultrasonic vibration to the proximal end of the flexible member, the ultrasonic vibration being along the longitudinal axis of the flexible member;
   (c) sweeping a length of the flexible member through the biological material so that it emulsifies the biological material;
   wherein the ultrasonic vibration creates the transverse ultrasonic vibration along the length of the flexible member so that a plurality of transverse nodes and anti-nodes are formed along the length of the flexible member.

18. A method according to claim 17, wherein the ultrasonic generator produces an ultrasonic vibration in the range of about 20 khz to about 80 khz.

19. A method according to claim 17, wherein the ultrasonic generator produces an ultrasonic vibration of approximately 20 khz.

20. A method according to claim 19, wherein a length of the flexible member is chosen so that eight nodes are produced along the length of the flexible member.

21. A method according to one of claims 17–20, wherein the flexible member is a thin, flexible member capable of being deflected and articulated.

22. A method according to claim 17, wherein the flexible member is formed of one of the following materials: titanium, aluminum, or steel.

23. A method according to claim 17, wherein the flexible member has a circular cross-section.

24. A method according to claim 23, wherein the flexible member has a diameter of less than about 1 mm.

25. A method according to claim 23, wherein the flexible member has a diameter of about 0.020 inches.

26. A method according to claim 23, wherein the flexible member has a diameter of about 0.030 inches.

27. A method according to claim 17, wherein the flexible member has a square cross-section.

28. A method according to claim 17, wherein the flexible member has a rectangular cross-section.

29. A method according to claim 17, wherein the flexible member has an elliptical cross-section.

30. A method according to claim 17, wherein the flexural stiffness of the flexible member is in the range of about $2.5 \times 10^7$ N/m to about $8.5 \times 10^7$ N/m.

31. A method according to claim 17, wherein the biological material is emulsified by the mechanism of cavitation.

32. A method according to claim 17, wherein the biological material is emulsified by mechanical action.

33. A method according to claim 17, wherein the flexible member has an area of the biological material destroying effect greater than a cross-sectional area of the flexible member.

34. The method of claim 17 wherein the biological material is a tissue.

35. A method of destroying a biological material comprising the steps of:
   (a) providing a flexible member with a proximal end, a distal tip, and a longitudinal axis wherein the flexible member has a degree of stiffness which allows the flexible member to support a transverse ultrasonic vibration;
   (b) applying an ultrasonic vibration to the proximal end of the flexible member, the ultrasonic vibration being in the direction of the longitudinal axis of the flexible member;
   (c) generating a series of transverse nodes and anti-nodes along a length of the flexible member so that there is substantially no longitudinal motion of the distal tip; and
   (d) placing the length of the flexible member in communication with the biological material so that the length of the flexible member destroys the biological material.

36. A method according to claim 35, wherein the flexible member communicates with the biological material through a fluid, and the flexible member causes cavitation which destroys the biological material.

37. The method of claim 35 wherein the biological material is a tissue.

38. A method of treating a biological material comprising steps of:
   (a) providing a flexible member with a longitudinal axis, a distal end, and a proximal end wherein the flexible member has a degree of stiffness which allows the flexible member to support a transverse ultrasonic vibration;
   (b) generating the transverse ultrasonic vibration in a length of the flexible member so that a plurality of transverse nodes and anti-nodes are formed along the length of the flexible member; and
   (c) placing the length of the flexible member into communication with the biological material so that the biological material is destroyed.

39. A method according to claim 38, wherein the flexible member causes cavitation in a fluid in contact with the biological material so that the biological material is destroyed by cavitation.

40. A method according to claim 38 or 39, wherein the step of generating the transverse ultrasonic vibration in the length of the flexible member is accomplished by providing an ultrasonic vibration to the proximal end of the flexible member.

41. A method according to claim 40, wherein the ultrasonic vibration has a frequency in the range of about 20 kHz to about 80 kHz.

42. A method according to one of claims 38–39, wherein there is substantially no longitudinal motion at the distal end of the flexible member.

43. The method of claim 38 wherein the biological material is a tissue.

44. A method of operating an ultrasonic medical device, comprising the steps of:
   (a) providing a flexible member with a proximal end, a distal end, and a longitudinal axis wherein the flexible member has a degree of stiffness which allows the flexible member to support a transverse ultrasonic vibration;
   (b) providing an ultrasonic generator to apply an ultrasonic vibration to the proximal end of the flexible member, the ultrasonic vibration being along the longitudinal axis of the flexible member;
   (c) controlling the amplitude and frequency of the ultrasonic vibration to produce the transverse ultrasonic vibration in the flexible member; and
   (d) producing a plurality of nodes and anti-nodes along a length of the flexible member wherein more than one of the plurality of transverse anti-nodes are in communication with a biological material.

45. A method according to claim 44, wherein the frequency is in the range of about 20 kHz to about 80 kHz.

46. A method according to claim 45, wherein the amplitude is in the range of about 150 microns to about 350 microns.

47. A method according to claim 44, wherein the amplitude is in the range of about 150 microns to about 350 microns.

48. A method according to claim 44, wherein the length of the flexible member is placed into contact with fluid in contact with the biological material so that the biological material is destroyed by cavitation.

49. A method according to one of claim 44, 45, 46 or 47 wherein there is substantially no longitudinal motion at the distal end of the flexible member.

50. An ultrasonic device comprising:

a flexible member with a longitudinal axis, a proximal end, and a distal end wherein the flexible member has a degree of stiffness which allows the flexible member to support a transverse ultrasonic vibration; and an ultrasonic generator coupled to the proximal end of the flexible member, the generator creating ultrasonic vibrations in the direction of the longitudinal axis of the flexible member, wherein a length and a cross-section of the flexible member are sized so that the ultrasonic vibrations are converted into the transverse ultrasonic vibration with a plurality of transverse nodes and anti-nodes along at least a portion of the length of the flexible member, and there is substantially no motion along the longitudinal axis at the distal end of the flexible member, wherein more than one of the plurality of transverse anti-nodes are in communication with a biological material.

51. A device according to claim 50, further comprising:

a series of transformer sections located between the ultrasonic generator and the flexible member, the transformer sections modifying the amplitude of the ultrasonic vibrations.

52. A device according to one of claim 50 or 51, further comprising:

a control device connected to the ultrasonic generator to control the frequency and amplitude of the generated vibrations.

53. A device according to one of claim 50 or 51, further comprising a sheath surrounding the transformer sections and a portion of the flexible member.

54. A device according to claim 53, wherein the sheath includes irrigation channels.

55. A device according to claim 53, wherein the sheath includes aspiration channels.

56. A device according to claim 53, wherein the sheath includes irrigation and aspiration channels.

57. A device according to claim 53, wherein the sheath and the flexible member are axially displaceable with one another so that a varying number of nodes are exposed.

* * * * *